United States Patent
Pierce, III et al.

(10) Patent No.: US 9,546,960 B2
(45) Date of Patent: Jan. 17, 2017

(54) SYSTEM AND METHOD FOR ANALYSIS OF CANNABIS

(71) Applicant: Lightwave Science, Inc., Seattle, WA (US)

(72) Inventors: William Bryan Pierce, III, Tampa, FL (US); Jason D. Pierce, Tampa, FL (US)

(73) Assignee: Lightwave Science, Inc., Seattle, WA (US)

( * ) Notice: Subject to any disclaimer, the term of this patent is extended or adjusted under 35 U.S.C. 154(b) by 9 days.

(21) Appl. No.: 14/541,630

(22) Filed: Nov. 14, 2014

(65) Prior Publication Data

US 2016/0139055 A1   May 19, 2016

(51) Int. Cl.
| | | |
|---|---|---|
| *G01J 3/00* | (2006.01) | |
| *G01N 21/84* | (2006.01) | |
| *G01N 21/25* | (2006.01) | |
| *G01J 3/28* | (2006.01) | |
| *G01N 21/35* | (2014.01) | |
| *G01N 33/94* | (2006.01) | |
| *G01N 21/47* | (2006.01) | |

(52) U.S. Cl.
CPC ............ *G01N 21/84* (2013.01); *G01J 3/2803* (2013.01); *G01N 21/255* (2013.01); *G01N 21/35* (2013.01); *G01N 33/948* (2013.01); *G01N 2021/4742* (2013.01); *G01N 2021/8466* (2013.01); *G01N 2201/0221* (2013.01); *G01N 2201/0692* (2013.01); *G01N 2201/0833* (2013.01); *G01N 2201/129* (2013.01)

(58) Field of Classification Search
CPC ............ G01N 21/84; G01N 21/42; G01J 3/28; G01J 3/02; G01J 3/42
USPC ................................................. 356/300–445
See application file for complete search history.

(56) References Cited

U.S. PATENT DOCUMENTS

| | | | | |
|---|---|---|---|---|
| 5,378,889 | A | * | 1/1995 | Lawrence ............. G01M 3/047 250/227.16 |
| 8,101,915 | B2 | | 1/2012 | McGill et al. |
| 8,421,017 | B2 | * | 4/2013 | McGill .................. G01N 21/64 250/338.5 |
| 8,421,018 | B2 | | 4/2013 | McGill et al. |
| 8,699,020 | B1 | | 4/2014 | Zhou et al. |
| 2002/0011567 | A1 | * | 1/2002 | Ozanich .................... G01J 3/02 250/326 |
| 2003/0179379 | A1 | * | 9/2003 | Gedig ................... G01N 21/553 356/445 |
| 2007/0192850 | A1 | * | 8/2007 | Cowburn ........... G06K 7/10762 726/20 |

* cited by examiner

*Primary Examiner* — Abdullahi Nur
(74) *Attorney, Agent, or Firm* — Greenberg Traurig, LLP

(57) ABSTRACT

A system including a light source, sampling tray, and at least three detectors mounted at angles with respect to each other receives light reflected from a sample of cannabis-based matter. Light from the three detectors is fed to a spectrometer which converts the reflected light into a fingerprint corresponding to the concentration of at least one substance in the sample. The fingerprint is processed by a statistical model to determine concentration level of the at least one substance in the sample and the concentration level is then displayed.

5 Claims, 5 Drawing Sheets

SYSTEM AND METHOD FOR ANALYSIS OF CANNABIS

FIELD

This invention relates to the field of plant analysis and more particularly to an apparatus, system, and method for analyzing components of cannabis.

BACKGROUND

Analysis of cannabis-based plant matter for content of certain substances are often required to determine the usefulness, potency, effectiveness, and value of the cannabis-based plant matter. It is not generally possible to determine the content of certain substances and, hence, potential medicinal value of a certain amount of cannabis-based plant matter through color, taste, touch, or smell. Furthermore, it is desirable to determine the presence of impurities such as mold or pesticides in the cannabis-based plant matter, especially if users are allergic to such.

Tetrahydrocannabinol (or THC), is the chemical responsible for most of cannabis' (marijuana's) psychological effects. In general, the value of a given quantity of a cannabis-based plant matter is somewhat proportional to the percentage of tetrahydrocannabinol in that cannabis. This is because the lower the THC content in the cannabis-based plant matter, the more the user needs to consume to produce the desired effects. Likewise, the CBD (CannaBiDol) content in the cannabis-based plant matter is significant because this component is known to have significant medical benefits. Another substance found in cannabis-based plant matter is terpenes, also known as aromic terpenes. These compounds give the cannabis a unique smell. Terpenes are oily, volatile molecules that evaporate easily. Some 20,000 terpenes have been identified and characterized by their molecular structure, around 200 of which have been found in cannabis. Many terpenes have medicinal benefits such as Alpha-pinene (essential pine oil) which is often found in cannabis. Alpha-pinene is a bronchodilator potentially helpful for asthmatics. Pinene is also known to promote alertness and memory retention.

The percentage of CBD is a given amount of cannabis-based plant matter can vary from almost zero (approximately 0.3% for some forms of hemp), but typically between 1 percent and 5 percent CBD. So, if a consumer consumes a certain amount of cannabis having 5% CBD, it would take approximately five times that amount of the cannabis-based plant matter having 1% CBD to achieve the same desired medicinal effect and, therefore, the value of this range of product varies with CBD concentration.

Given that there is no real way to determine the value of a given amount of cannabis-based plant matter by taste, smell, color, texture, etc., it is difficult for consumers and marketers to understand what they are buying or selling. With alcohol, the consumer is notified of the percentage of alcohol as a percentage or "proof" measurement that is printed on the bottle such as 14.5% for a certain bottle of wine or 80 proof (i.e., 40%) for a certain bottle of vodka.

Being that the CBD content of cannabis-based plant matter is determined by many factors such as growing conditions (e.g., soil, light, water, fertilizer), plant lineage (e.g., genetic makeup), growing time, plant maturity, drying, etc., there is a need to measure the many different compounds that are within a sample of cannabis-based plant matter.

What is needed is a portable system that will provide a direct value at least one concentration of a substance in a sample of cannabis-based plant matter.

SUMMARY

In one embodiment, a portable cannabis sampling system is disclosed including a portable enclosure with a stabilized light source mounted in the portable enclosure for delivering light to a cannabis-based sample. The cannabis-based sample is in communication with the stabilized light source and light from the stabilized light source diffuse scattering from the cannabis-based sample. Pluralities of sensors are interfaced to the portable enclosure and are offset from each other by an angle. The sensors collect the diffused and scattered light from the cannabis-based sample. The system also includes a plurality of fiber optics, each one connected to a corresponding one of the sensors and each one connected to a spectrometer that receives the diffused and scattered light from the fiber optics that is offset by the angles and converts the diffused and scattered light into an array of numeric values that represents a fingerprint of substances within the cannabis-based sample.

In another embodiment, a method of measuring at least one substance in a cannabis-based sample is disclosed including for each sample of a plurality of historical cannabis-based samples, collecting a fingerprint for the each sample by exposing the each sample to a source of light, gathering reflected light that has been reflected from the each sample from at least three angles, transmitting the reflected light to a spectrometer, and generating the fingerprint from the reflected light by the spectrometer. Now, the concentration of at least one substance within the each sample is measured (e.g., sent to a laboratory for analysis, recording the result) and the fingerprint is associated with the concentration of the at least one substance in a database. After several fingerprints and associated concentration levels have been recorded, at least one statistical model is created based on the fingerprints and the concentration of at least one substance. Now to determine concentration levels of any of the at least one substance in an unknown sample of cannabis-based matter, a new fingerprint is captured from the unknown sample of cannabis-based matter by exposing the unknown sample of cannabis-based matter to the source of light, gathering reflected light from at least three angles (the light reflected from the unknown sample of cannabis-based matter), transmitting the reflected light to the spectrometer, and generating the new fingerprint from the reflected light by the spectrometer. Next, a concentration value for the at least one substance in the unknown sample of cannabis-based matter is determined by running the at least one statistical model against the new fingerprint and the concentration value for the at least one substance in the cannabis-based sample is displayed.

In another embodiment, a portable cannabis sampling system is disclosed including a portable enclosure with a stabilized light source mounted in the portable enclosure for delivering light to a cannabis-based sample. The cannabis-based sample is in communication with the stabilized light source and light from the stabilized light source diffuses/scatters from the cannabis-based sample. There are three sensors, each sensor being offset from each other by 120 degrees, and each of the sensors collect the diffused and scattered light from the cannabis-based sample. Each of three fiber optics is connected to a corresponding one of the three sensors and a spectrometer receives the diffused and scattered light from the three fiber optics and converts the diffused and scattered light into a fingerprint that represent concentrations of substances in the cannabis-based sample.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
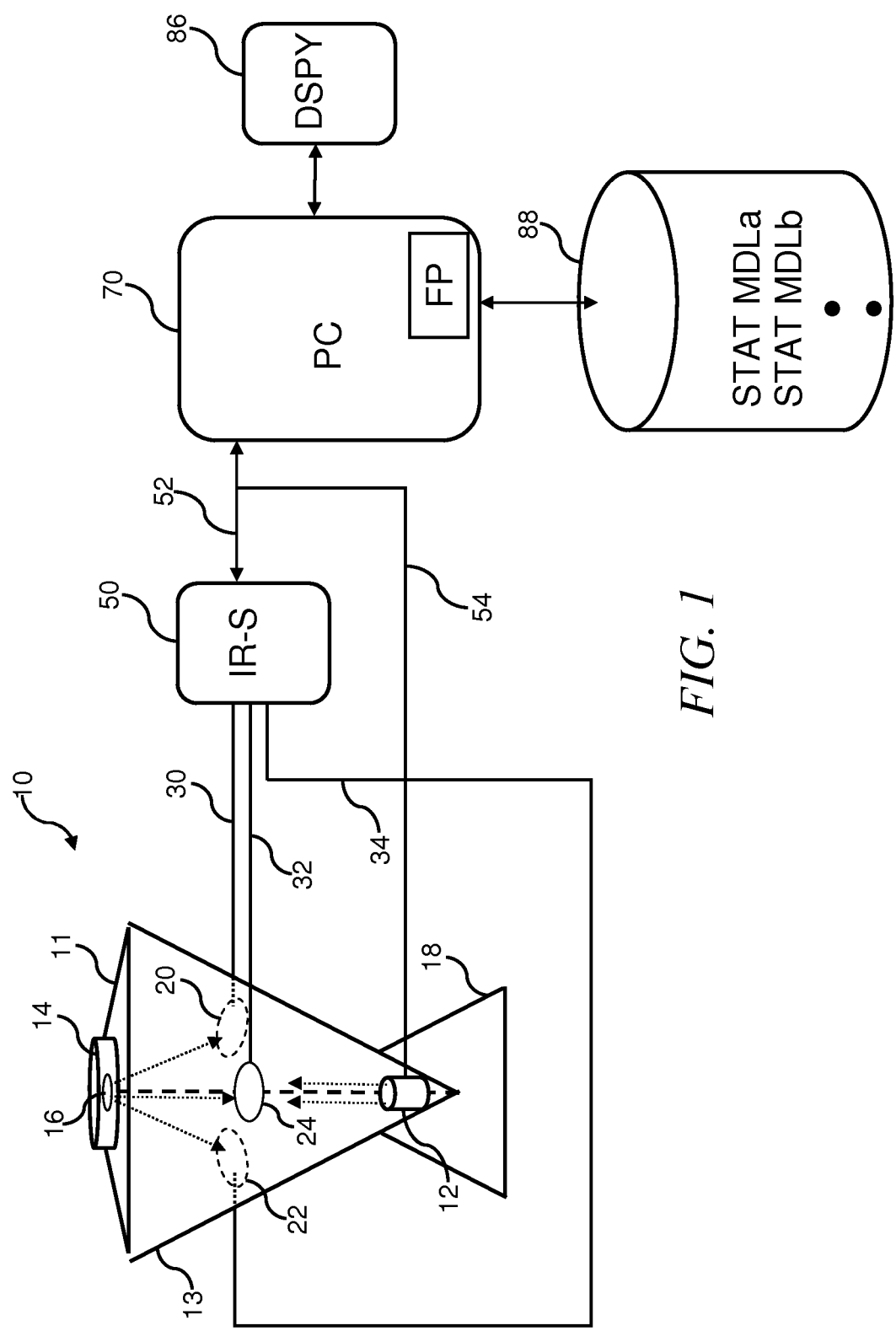
FIG. 1 illustrates a plan view of a system for analyzing samples of cannabis-based plant matter.

Reference will now be made in detail to the presently preferred embodiments of the invention, examples of which are illustrated in the accompanying drawings. Throughout the following detailed description, the same reference numerals refer to the same elements in all figures.

The herbaceous plant cannabis is grown, processed, and utilized in the United States under Government regulations and controlled by Government agencies, and in some states permitted for recreational and/or medical use. Research is often performed under the control of Federal Agencies, and evaluation as to the use of the drug as a therapeutic pharmaceutical is being performed in the medical field. It is also known that cannabis is legally used as a euphoriant in certain geographic areas or states.

Referring to FIG. 1, a plan view of a system for analyzing samples of cannabis-based plant matter is shown. In many scenarios, it is valuable to obtain a measurement of the level of certain substances within a sample of cannabis-based plant matter. For example, during the drying of the plant, and during the purchase/sale of a quantity of the plant or plant extract, it is valuable to know the percentage of available substances such as tetrahydrocannabinol (THC), tetrahydrocannabinolic acid (THCA), cannabidiol (CBD), cannabidiolic acid (CBDA), cannabinol (CBN), moisture, mold, and to a lesser extent, protein, fat, etc. Further, for medicinal reasons, it is valuable to know the concentration of various terpenes, for example Alpha-pinene, Myrcene, Limonene, Linalool, and Beta-caryophyllene.

As an example, purchasing 10 g of cannabis (assuming all percentages of other components are equal) having a 10% moisture content is better than purchasing 10 g of cannabis-based plant matter having a 20% moisture content, being that since you are purchasing by weight, you are paying for the weight of the water in the product you are buying.

To understand concentrations of various substances within a cannabis-based plant prior to the present invention, a sample of the cannabis-based plant needed to be shipped to a laboratory for full analysis by gas chromatography or by liquid chromatography, but several issues arise from doing such. First, the round trip to the laboratory takes time and the opportunity for purchase/sale may wane while waiting for results. Second, the cannabis will change characteristics and content during the shipping to the laboratory. For example, moisture evaporates and mold grows/increases. Third, the cost of gas chromatography and liquid chromatography analysis is often very high, and fourth, due to individual laws of certain locations, the transport of cannabis outside of certain areas is often illegal. Therefore, there is a significant advantage to perform field analysis on many different types of cannabis-based plant matter.

As described, in laboratory analysis of cannabis-based plant matter, performance a full gas chromatography or liquid chromatography analysis on a sample of the cannabis-based plant matter is required for each component (e.g., one analysis for THC, another for CBD, etc.). The output of each analysis is a listing of all component substances of the sample cannabis-based plant matter based on GC standards/methods/procedures or LC standards/methods/procedures which are different even between different Labs. Often, a few days are required to perform this analysis, plus shipping time.

Instead, there is an advantage in comparing to hundreds of previously measured samples of cannabis-based plant matter and producing a value that is relative to each of the prior samples instead of providing the grower, seller, buyer, or user with data that can vary between laboratories performing the testing. The disclosed system does such, by capturing numerical arrays (i.e., fingerprints of molecules) of measurements related to each of a set of cannabis-based plant matter and associating those numerical arrays with an actual analysis of the targeted substances in each of the set of cannabis-based plant matter, for example, by gas chromatography or by liquid chromatography. From this set of data, a statistical model is built. Then, when a new fingerprint (numerical array) for an unknown sample of cannabis-based plant matter is captured, this statistical model is used to evaluate the unknown sample of cannabis-based plant matter and report values for specific compounds. In a simplistic example in which only THC content is of interest, assume ten spectrographic samples are collected from ten different samples of cannabis-based plant matter, each sample having a fingerprint (spectral chart) and an associated THC content value that is obtained by other means (e.g., by gas chromatography, by liquid chromatography, using "statistically confirmed" reference standards and procedures). From these ten fingerprints and associated THC content values, a statistical model is built using, for example, available MATLAB software programs that applies weighting factors to numerical array fingerprints that correctly yields the known THC concentration for each future sample. There are many math packages known that will produce a statistical model given a set of data (e.g. a set of fingerprints) using, for example, MATLAB functions for chemometric calibration. Such packages are well known from various companies such as MathWorks®, Camo, InfoMetrix®, etc. These packages are intended for use with analytical instruments in the analysis of large datasets.

Now, when a new, unknown sample of cannabis-based plant matter is spectrally measured yielding a new fingerprint (spectral array), this fingerprint of cannabis-based plant matter is then processed by the statistical model and a THC value of the unknown sample of cannabis-based plant matter is determined, then stored, printed, and/or displayed. Again, THC is used in this description as an example and any of the possible substances available in cannabis-based plant matter are modeled and later analyzed in the same manner, for example, tetrahydrocannabinol (THC), tetrahydrocannabinolic acid (THCA), cannabidiol (CBD), cannabidiolic acid (CBDA), cannabinol (CBN), moisture, mold, protein, fat, terpenes (e.g., Alpha-pinene, Myrcene, Limonene, Linalool, and Beta-caryophyllene), etc.

In the exemplary cannabis-based plant matter sampling system 10 of FIG. 1, multiple angled sides 13 are aimed toward the top surface 11 on which the sampling cup 14 rests. The cannabis-based plant matter sample 16 is placed in the sampling cup 14 which is in optical communication with a light source 12. Light from the light source 12 is directed onto the sample 16 and reflects off the sample 16 onto a plurality of receptors 20/22/24 for gathering light. Each of the receptors 20/22/24 are positioned on one of the angled sides 13 of the cannabis-based plant matter sampling system 10. The light then travels through the fiber optics 30/32/34 to a spectrometer 50 (e.g. an infrared spectrometer 50). The spectrometer 50 creates a multi-dimensional image of the light from the plurality of receptors 20/22/24. Although many different light sources 12 are anticipated with narrow or wide spectrums of emitted light, it is preferred that the light source 12 emit light in the range of 900 to 2300 nanometers.

The three-dimensional image of the light (i.e., a fingerprint of the cannabis-based plant material) is then transferred to a computer system 70 through, for example, a serial interface 52 such as a USB interface 52, though any known or future interface 52 is anticipated. In some embodiments, the interface 52, and hence the computer system 70, provides power to the light source 12, while in other embodiment, power is provided for the light source in other ways such as from a power supply, battery, solar panel, etc. The computer system 70 has at least a display 86 for displaying results of the analysis and some form of storage 88 for storing software and models required to analyze each sampling. It is estimated that the analysis of a sample is possible within 30 seconds with around a 1% accuracy.

In contrast to general-purpose, large and expensive gas chromatography or liquid chromatography systems, the disclosed invention provides direct readings of key compounds typically found in cannabis-based plant matter such as tetrahydrocannabinol (THC), tetrahydrocannabinolic acid (THCA), cannabidiol (CBD), cannabidiolic acid (CBDA), cannabinol (CBN), terpenes, moisture, and mold. For example, instead of presenting a frequency vs molecular absorption chart of substance concentrations, a list of percentages is displayed on the display 86 of the computer system 70. For example, if 3% THC, 21% moisture, and 1% mold is measured, then a message as: "3% THC, 21% H2O, 1% mold" is displayed on the display 86 of the computer system 70, this data being what is important to the grower, store owner, and the consumer.

In some embodiments, to support the cannabis-based plant matter sampling system 10, a fixture 18 is included having a substantially flat bottom for supporting the cannabis-based plant matter sampling system 10 on, for example, a table or other surface.

Figure 2:
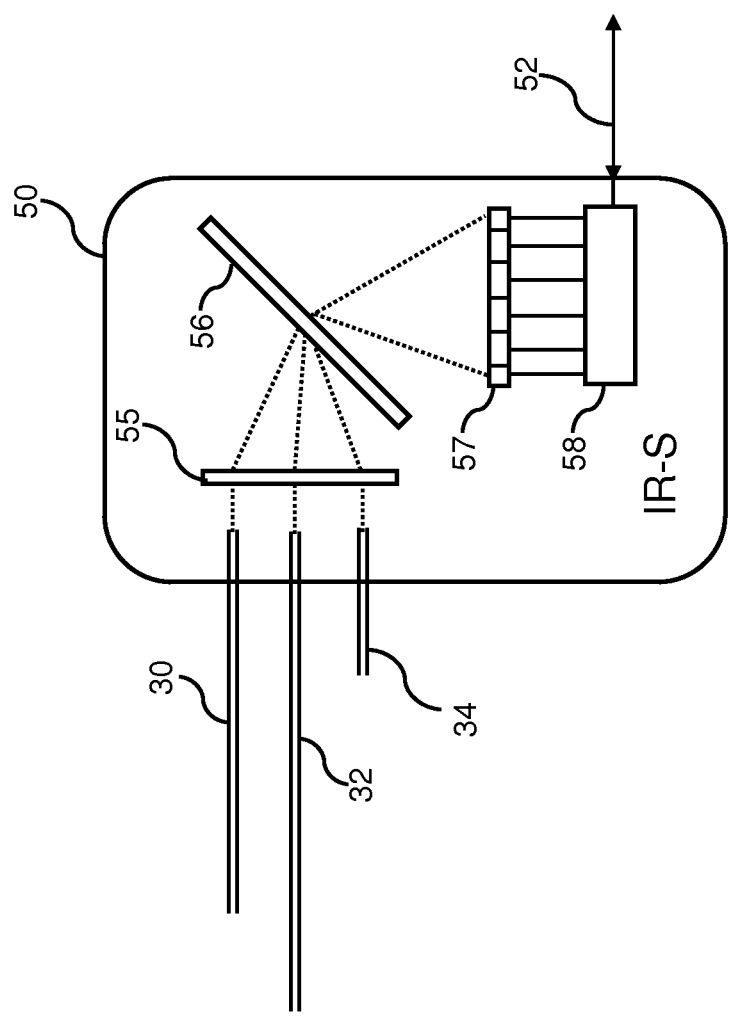
FIG. 2 illustrates a plan view of an exemplary spectral analysis device of the system for analyzing samples of cannabis-based plant matter.

FIG. 2, a plan view of an exemplary spectral analysis device 50 is shown. In this, the light that is reflected from the cannabis-based plant matter sample 16 is received at multiple angles (three angles in this example though any number of angles is anticipated). The light is transmitted through the fiber optic tubes 30/32/34 (again, three in this example), and the light is aimed at one or more filters 56 by one or more lenses 55, resulting in the various elements of a photo detection array 57 being illuminated at individual intensities proportional to certain characteristics of the cannabis sample 16. Although many photo detection arrays 57 are anticipated, examples of a photo detection array 57 include a photo-diode array 57 and/or what is known as a charge-coupled device 57 often called a CCD 57. In general, the photo detection array 57 receives an intensity of light at each element dependent upon the composition of various chemicals in the cannabis sample 16. The photo detection array 57 converts each light intensity to an electrical value that is detected by logic 58 and converted into, for example, an array of digital values (i.e., the fingerprint of the cannabis-based plant matter sample 16) that is then transmitted to the computer system 70 (see FIG. 1) over an interface 52, for example, a USB interface 52. This array of digital values represents the fingerprint of the current cannabis-based plant matter sample 16.

Figure 3:
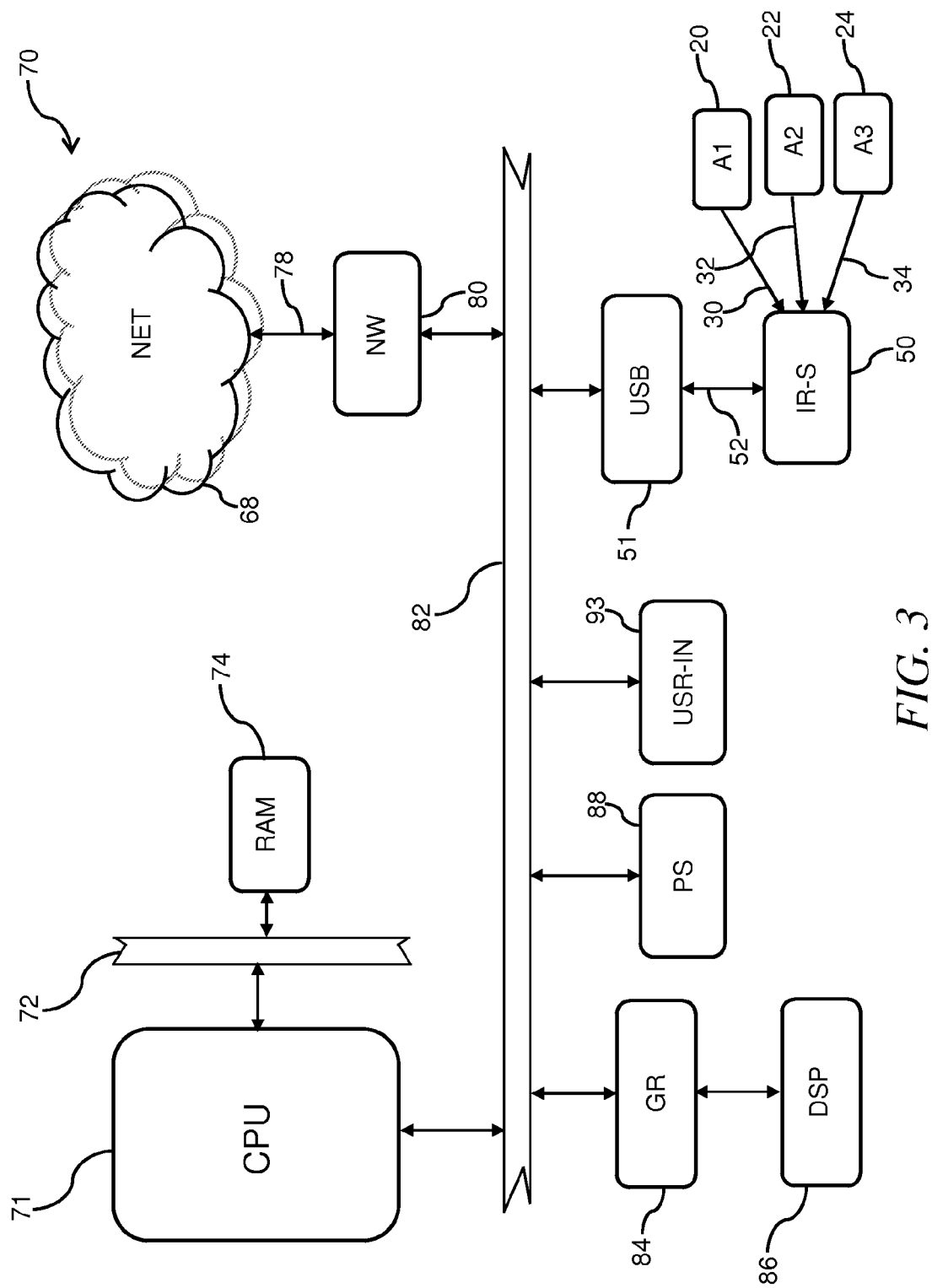
FIG. 3 illustrates a schematic view of a typical computer system with spectral analysis.

Referring to FIG. 3, a schematic view of a typical computer system with spectral analysis 70 is shown. The exemplary computer system with spectral analysis 70 utilizes any known processor-based system. This exemplary computer system with spectral analysis 70 is shown in its simplest form. Different architectures are known that accomplish similar results in a similar fashion and the present invention is not limited in any way to any particular computer system with spectral analysis 70 architecture or implementation. In this exemplary computer system with spectral analysis 70, a processor 71 executes or runs programs from a memory 74. The programs that measure the sample 16 are generally loaded into the random access memory 74 when needed. The processor 71 is any known or future processor, typically a processor 71 as typically used in notebook computers, tablet computers, cellular phones, and the like. The random access memory 74 is typically connected to the processor 71 by, for example, a memory bus 72. The random access memory 74 is any memory 74 suitable for connection and operation with the selected processor 71, such as SRAM, DRAM, SDRAM, RDRAM, DDR, DDR-2, etc.

Also connected to the processor 71 is a system bus 82 for interfacing with peripheral subsystems such as a network interface 80 and a graphics adapter 84. The graphics adapter 84 receives commands from the processor 70 and controls what is depicted on a display image on the display 86, including status messages and analysis output.

In general, persistent storage 88 stores operating procedures, control data, programs, etc., as known in the industry. It is anticipated that algorithms and statistical models that are used to calculate values related to the sample 16 are stored in the persistent storage 88.

The peripherals shown are examples and other peripherals are known in the industry such as speakers, microphones, USB interfaces, Bluetooth transceivers, Wi-Fi transceivers, touch screen inputs, image sensors, temperature sensors, etc., the likes of which are not shown for brevity and clarity reasons.

The network interface 80 connects the computer system with spectral analysis 70 to other systems for various purposes such as uploading new fingerprints along with measured contents and downloading of models and updated models, etc.

The computer system with spectral analysis 70 communicates with the spectral analysis subsystem 50 through any known communication system, for example, as shown, a USB port 51 and a USB connection 52. Many different communication systems are anticipated and the simplified USB port is one example as using any form of data communication to the spectral analysis subsystem 50, including, but not limited to any of the various known digital and analog interfaces such as NRZ (non-return to zero), RS-232, I2C, IIC, etc. In some embodiments, a wireless interface such as near-filed or Bluetooth is used.

The computer system with spectral analysis 70 typically has one or more user controls 93 such as touch screen inputs, keyboards, joysticks, mice, etc., through which the operation of the disclosed applications and algorithms are initiated and controlled.

Figure 4:
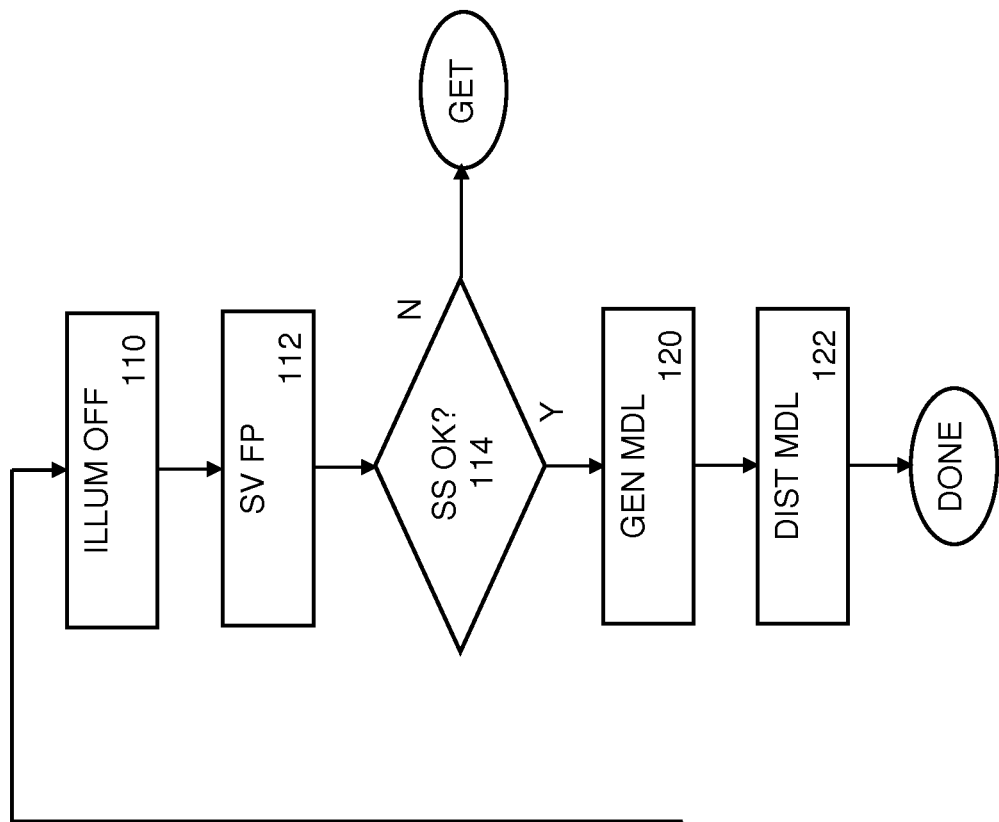
FIG. 4 illustrates a program flow of the system for generating a statistical model for the analysis of cannabis-based plant matter.
Figure 4:
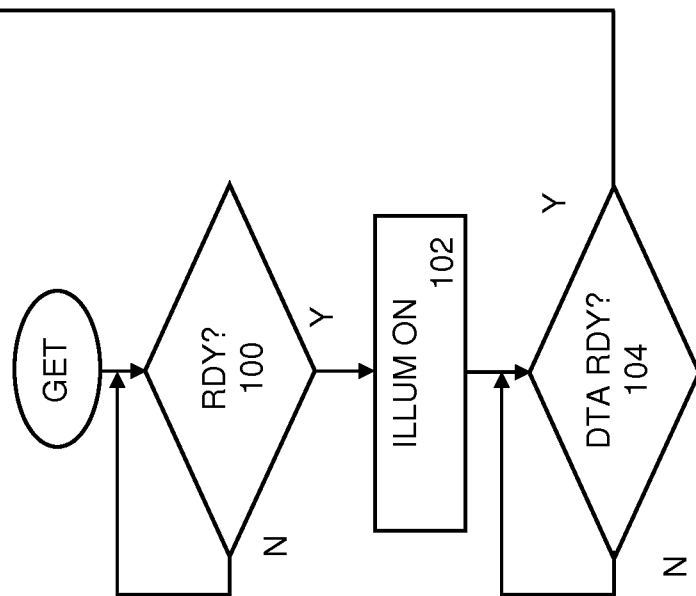

Referring to FIG. 4, a program flow of the system for analyzing known samples of cannabis-based plant matter an generating a statistical model of such samples is shown. This is an example of one such program flow that operates in the computer system 70 with interaction with the cannabis-based plant matter sampling system 10 to present a direct reading of one or more contents of the cannabis-based plant matter sample 16.

Although the description below shows data gathering operations using one system for analyzing known samples of cannabis-based plant matter, it is fully anticipated that fingerprints and data are collected from many similar systems for analyzing known samples of cannabis-based plant matter and that each set of fingerprints and data contribute further to the accuracy of the developed statistical models.

The creation of the statistical model requires multiple cannabis-based plant matter sample 16 that have been or are to be analyzed by other means (e.g., by gas chromatography or by liquid chromatography). The exemplary flow begins with preparation and possible self-tests to determine if the cannabis-based plant matter sampling system 10 is ready to use 100. Once the cannabis-based plant matter sampling system 10 is ready 100, the light source 12 is energized 102 to emit light, for example, a broad spectrum of light is emitted in the range of 900 to 2300 nanometers. The light is directed at the cannabis-based plant matter sample 16 and some of the light is reflected and received into the plurality of fiber optics 30/32/34 at a plurality of angles. For example, three such angles and fiber optics 30/32/34 are shown in FIGS. 1 and 2. The received light is transmitted to the spectrometer 50, which is any spectrometer 50. In this exemplary spectrometer 50, the light is refracted and aimed at a detector array 57/58 where the various intensities of light at each element of the detector array 57/58 is converted into an electrical signal, then into a numeric value, resulting in an array of numeric values that represents a fingerprint of the composition of the cannabis-based plant matter sample 16.

Once the array of numeric values is received 104, in some embodiments, the light source 12 is shut off 110 and the array of number values is saved 112. In this, the numeric array of values is used as a fingerprint and is associated with an actual set of measured values that are independently derived from the sample of cannabis-based plant matter 16 (e.g., measured by gas chromatography or by liquid chromatography).

Next, it is determined if enough fingerprints and analyzed results have been collected 114 and, if not, the above steps are repeated to obtain more fingerprints and analyzed results. Once sufficient fingerprints have been collected 114, statistical models are generated 120 based upon this set of fingerprints and the associated values of various components reported from analysis of each sample of cannabis-based plant matter 16. The resulting statistical models are then distributed 122 to one or more systems for analyzing samples of cannabis-based plant.

Note, as further fingerprints are captured from new samples of cannabis-based plant matter 16, along with analysis of such, the above steps are repeated to generate updated statistical models, typically having greater accuracy, and these statistical models are then distributed 122 to one or more systems for analyzing samples of cannabis-based plant matter.

Figure 5:
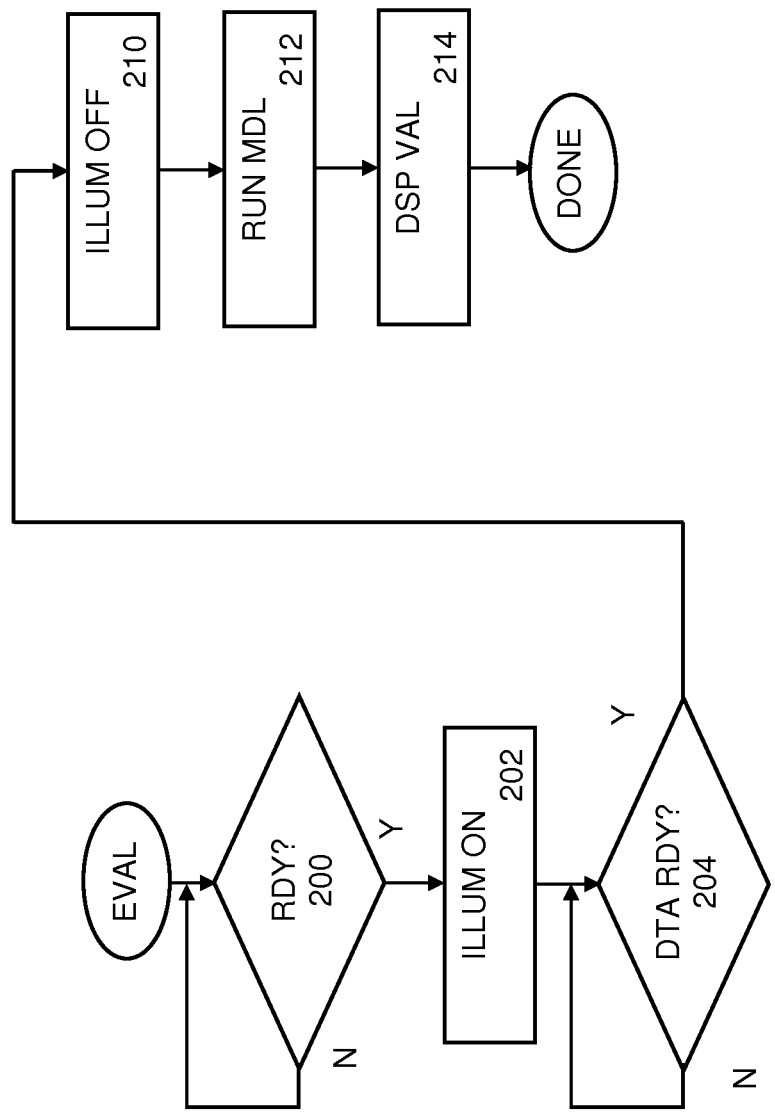
FIG. 5 illustrates a program flow of the system for analyzing samples of cannabis-based plant matter using the statistical model.

Referring to FIG. 5, a program flow of the system for analyzing samples of cannabis-based plant matter is shown. This is an example of one such program flow that operates in the computer system 70 with interaction with the cannabis-based plant matter sampling system 10 to present a direct reading of one or more contents of the cannabis-based plant matter sample 16.

The exemplary flow begins with preparation and possible self-tests to determine if the cannabis-based plant matter sampling system 10 is ready to use 200. Once the cannabis-based plant matter sampling system 10 is ready 200, the light source 12 is energized 202 to emit light, for example, a broad spectrum of light is emitted in the range of 900 to 2300 nanometers. The light is directed at the cannabis-based plant matter sample 16 and some of the light is reflected and received into the plurality of fiber optics 30/32/34 at a plurality of angles. For example, three such angles and three fiber optics 30/32/34 are shown in FIGS. 1 and 2. The received light is transmitted to the spectrometer 50, which is any spectrometer 50. In this exemplary spectrometer 50, the light is refracted and aimed at a detector array 57/58 where the various intensities of light at each element of the detector array 57/58 is converted into an electrical signal, then into a numeric value, resulting in an array of numeric values that represents a fingerprint of the composition of the cannabis-based plant matter sample 16.

Once the array of numeric values (fingerprint) is captured 204, the light source 12 is optionally shut off 210 and the fingerprint is processed 212 by the one or more statistical models previously generated (see FIG. 4). The statistical model(s) determine a concentration (or presence) of one or more specific substances within the cannabis-based plant matter sample 16. In this, the fingerprint is processed by one or more statistical models (e.g., a model that was generated as in FIG. 4) to determine the values of the specific substances of the sample 16. One exemplary statistical model is a curve fitting algorithm such as Partial Least Square (PLS) algorithms to find where the array of number values (fingerprint) for the sample 16 fits within a statistical model generated using the plurality of previous known samples of the cannabis-based plant matter (as in FIG. 4). From this statistical model 212, numeric values for one or more targeted substances of the cannabis-based plant matter sample 16 is calculated. Preferably, the numeric values for each targeted substances is then displayed 214, for example on the display 86 (see FIGS. 1 and 3). For example, one exemplary numerical value that is displayed is the percentage of tetrahydrocannabinol (THC) present in the cannabis-based plant matter sample (e.g., "The sample contains 2.9% THC").

Again, as more and more new samples of the cannabis-based plant matter are captured using this methods of FIG. 4, the database is improved with the new samples and updated statistical models are created from the database and distributed to one or more of the cannabis-based plant matter sampling systems 10, thereby improving the accuracy of each the cannabis-based plant matter sampling system 10.

The cannabis-based plant matter sampling system 10 measures any forms or classes of cannabis and/or products containing cannabis, typically dried or processed, including plant form (leaves, buds, etc.), extracts, waxes, oils, edible products containing cannabis, etc. It is fully anticipated that, for each class of cannabis-based plant matter, a different statistical model is created and provided for use in measuring samples 16 of that class of cannabis-based plant matter. For example, to measure the amount of THC in a cookie containing cannabis, a piece of the cookie that contains cannabis is placed in the sampling dish 14 and the above process 200-214 is performed using a statistical model that was generated using known samples of that class of cannabis-based cookies. This statistical model was created by measuring several known samples of this class of cannabis-based products as above and capturing the numeric array that represents this sample (fingerprint), then analyzing this sample in the laboratory and associating the results of this analysis with the numeric array. From this, the statistical model for cookies containing cannabis is generated and distributed to other cannabis-based plant matter sampling systems 10.

In order to develop larger libraries of known samples, it is anticipated that the manufacturer of the cannabis-based plant matter sampling system 10 will request users of existing cannabis-based plant matter sampling systems 10 to provide numeric arrays (i.e., fingerprints) of samples along with the laboratory analysis of the samples to the manufacturer for integration into databases and for generation of improved statistical models. For example, after receiving 20 samples, each having the numeric array (fingerprint) and laboratory measurement data, the manufacturer of the cannabis-based plant matter sampling systems 10 provides an additional month rental or other cash incentives.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A method of measuring at least one substance in a *cannabis*-based sample, the method comprising:
   for each sample of a plurality of historical *cannabis*-based samples:
   collecting a fingerprint for the each sample by exposing the each sample to a source of light, gathering reflected light from at least three angles, the reflected light having been reflected from the each sample, transmitting the reflected light to a spectrometer, and generating the fingerprint from the reflected light by the spectrometer;
   measuring the concentration of at least one substance within the each sample;
   associating the fingerprint with the concentration of the at least one substance in a database;
   generating at least one statistical model based on the fingerprints and the concentration of at least one substance;
   for each unknown sample of *cannabis*-based matter:
   collecting a new fingerprint for the unknown sample of *cannabis*-based matter by exposing the unknown sample of *cannabis*-based matter to the source of light, gathering reflected light from at least three angles, the reflected light having been reflected from the unknown sample of *cannabis*-based matter, transmitting the reflected light to the spectrometer, and generating the new fingerprint from the reflected light by the spectrometer;
   determining a concentration value for the at least one substance in the unknown sample of *cannabis*-based matter by running the at least one statistical model against the new fingerprint;
   displaying the concentration value for the at least one substance in the *cannabis*-based sample.

2. The method of claim 1, wherein the at least one statistical model is a Partial Least Square (PLS) algorithm.

3. The method of claim 1, wherein the at least one substance in the *cannabis*-based sample is selected from the set of substances comprising consisting of: tetrahydrocannabinol (THC), tetrahydrocannabinolic acid (THCA), cannabidiol (CBD), cannabidiolic acid (CBDA), cannabinol (CBN), moisture, and mold.

4. The method of claim 1, wherein the at least one substance in the *cannabis*-based sample is selected from available terpenes selected from the set of terpenes comprising Alpha-pinene, Myrcene, Limonene, Linalool, and Beta-caryophyllene.

5. The method of claim 1, wherein the source of light emits light at wavelengths in the range of 900 to 2300 nanometers.

* * * * *